United States Patent [19]

Umezawa et al.

[11] 4,065,495
[45] Dec. 27, 1977

[54] δ-SUBSTITUTED NEGAMYCIN DERIVATIVES AND SYNTHESES

[75] Inventors: Hamao Umezawa, Tokyo; Shinichi Kondo, Yokohama, both of Japan

[73] Assignee: Zaidan Hojin Biseibutsu Kagaku Kenkyu Kai, Japan

[21] Appl. No.: 735,352

[22] Filed: Oct. 26, 1976

[30] Foreign Application Priority Data

Nov. 11, 1975 Japan .............................. 50-134710
Jan. 1, 1976 Japan .............................. 51-000258

[51] Int. Cl.$^2$ .......................................... C07C 109/97
[52] U.S. Cl. ........................... 260/534 M; 260/207;
260/239.1; 260/293.51; 260/448 R; 260/456 A;
260/501.11; 260/534 R; 260/925; 424/316;
424/319; 560/49; 560/159; 560/169
[58] Field of Search ........................ 260/534 R, 534 M

[56] References Cited

U.S. PATENT DOCUMENTS

| | | | |
|---|---|---|---|
| 3,679,742 | 7/1972 | Umezawa et al. | 260/534 M |
| 3,743,580 | 7/1973 | Umezawa et al. | 260/534 M |
| 3,962,317 | 6/1976 | Curran | 260/534 R |

OTHER PUBLICATIONS

Kondo, J. Antibiot., 24(10), pp. 732-734 (1971).
Kondo, J. Antibiot., 29(2), pp. 208-211 (1976).
Kondo, N. Am. Chem. Soc., 93, p. 6305 (1971).
Shibahara, J. Am. Chem. Soc., 94, pp. 4353-4354 (1972).
Hamada, J. Antibiot., 23(3), pp. 170-171 (1970).
Hilgetag, "Preparative Organic Chemistry," pp. 62-64 & 368 (1972).
Uehara, J. Antibiot., 29(9) pp. 937-943 (1976).
Hickinbottom, "Reactions of Organic Compounds", pp. 510-517 & 532-533 (1962).

*Primary Examiner*—James O. Thomas, Jr.
*Assistant Examiner*—Michael Shippen
*Attorney, Agent, or Firm*—Herbert W. Taylor, Jr.

[57] ABSTRACT

Compounds having the structure

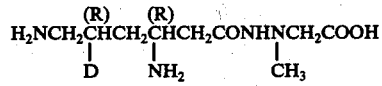

wherein D is hydrogen or methoxy were synthesized and found to be antibacterial agents.

3 Claims, No Drawings

δ-SUBSTITUTED NEGAMYCIN DERIVATIVES AND SYNTHESES

BACKGROUND OF THE INVENTION

1. Field of the Invention

The novel synthetic organic compounds of the present invention are antibacterial agents and are used as are other members of that class.

2. Description of the Prior Art

Negamycin is an antibiotic discovered by the present inventors (Japan 34827/1969, Japan 28835/1971) and is represented by the following formula (III):

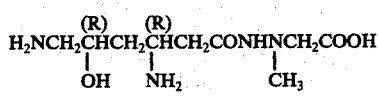

having a unique structure consisting of a hydrazide bond between (R,R)-δ-hydroxy-β-lysine (IV) and 1-methylhydrazinoacetic acid (V)

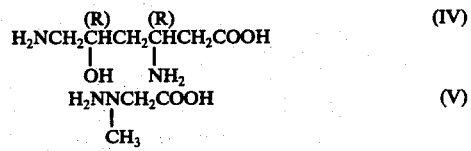

(J. Am. Chem. Soc. 93, 6305, 1971). In the above formulae, a symbol (R) is indicated and used for stereochemistry (Ref. "Nomenclature of Organic Compounds" ed. by J. H. Fletcher, O. C. Dermer and R. B. Fox, p. 103, American Chemical Society, Washington, D.C., 1974). See also U.S. Pat. Nos. 3,679,742 and 3,743,580 and M. Hamada et al., A New Antibiotic, Negamycin, J. Antibiotics, 23(3), 170–71 (1970).

SUMMARY OF THE INVENTION

The present invention provides new derivatives of negamycin, that is, semisynthetic antibiotics having the ability to inhibit Gram-positive and Gram-negative bacteria and being of quite stable character even in acidic aqueous solutions, which are represented by the following formula:

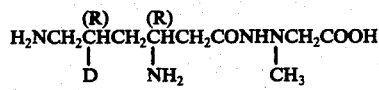

and the acid and base salts thereof, wherein D is selected from the group consisting of H (deoxynegamycin) and CH₃O-(O-methylnegamycin).

Salts of deoxynegamycin and O-methylnegamycin include carboxylic acid salts including nontoxic metallic salts such as sodium, potassium, calcium and aluminum, the ammonium salt and substituted ammonium salts, e.g. salts of such nontoxic amines as trialkylamines, including triethylamine, procaine, dibenzylamine, N-benzyl-β-phenethylamine, 1-ephenamine, N,N'-dibenzylethylenediamine, dehydroabietylamine, N,N'-bis-dehydroabietylethylenediamine, N-(lower)alkylpiperidine, e.g. N-ethylpiperidine and other amines which have been used to form salts with benzylpenicillin; and the nontoxic, acid addition salts thereof, (i.e. the amine salts) including the mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate and the like. Also included are the salts of deoxynegamycin and O-methylnegamycin with cinnamic acid, picric acid, p-hydroxyazobenzene-p'-sulfonic acid, phytic acid, livopimaric-6,6a-cis-endosuccinic acid, sulfamic acid and glycolic acid. For therapeutic purposes use is made of salts of nontoxic acids but salts of toxic acids, e.g. p-hydroxyazobenzene-p'-sulfonic acid, are useful in isolation procedures, e.g. as precipitants from aqueous solutions and for disinfectant purposes where toxicity is not important.

In the treatment of bacterial infections in animals, including man, the compounds of this invention are administered parenterally in accordance with conventional procedures for antibiotic administration in an amount of from about 5 to 200 mg./kg./day and preferably about 5 to 20 mg./kg./day in divided dosage, e.g. three to four times a day. They are administered in dosage units containing, for example, 125 or 250 or 500 mg. of active ingredient with suitable physiologically acceptable carriers or excipients. The dosage units are in the form of liquid preparations such as solutions or suspensions.

The compounds of the present invention are also used topically in the treatment of superficial infections such as infections of skin or mucous membrane. For this purpose use can be made of conventional ointments, (e.g. 1% or 5%) or solutions and suspensions in aqueous media at concentrations of 1% to 10%.

The present invention provides the synthesis of δ-substituted negamycins which are much more stable in aqueous solution than negamycin itself and have antibacterial activities. Thus, a constituent of negamycin, (R,R)-δ-hydroxy-β-lysine (IV), is converted to D-β-lysine by removing the hydroxyl group at δ-position or to (R,R)-δ-methoxy-β-lysine by replacing the hydroxyl group with a methoxyl group at δ position, and two amino groups in those derivatives are protected, the acid coupled with 1-methylhydrazinoacetic acid and the protective groups for the amino groups are then removed to yield the desired δ-substituted negamycin derivatives, deoxynegamycin or O-methylnegamycin as shown as formula (II) which are found to be quite stable in aqueous solution and active against Gram-positive and Gram-negative bacteria.

In one aspect of the present invention N,N'-di-protected-D-β-lysine (D = H in formula I) and N,N'-di-protected-(R,R)-δ-methoxy-β-lysine (D = —OCH₃ in formula I), which are represented by the following formula:

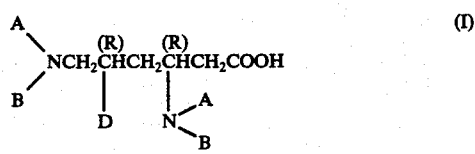

wherein A is hydrogen and B is a monovalent protective group for an amino group or A and B are one divalent protective group for an amino group and D is hydrogen or methoxyl, are separately coupled with 1-methylhydrazinoacetic acid and the protective groups removed to prepare deoxynegamycin (D = H in formula II) or O-methylnegamycin (D = —OCH₃ in formula II).

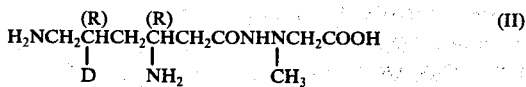

(II)

Starting materials (I'), D-β-lysine (D = H) and (R,R)-δ-methoxy-β-lysine (D = —OCH₃),

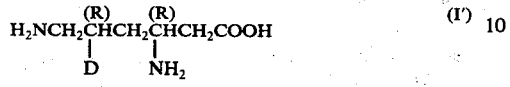

(I')

should be protected with known protective groups on their two amino groups. Although use can be made of the usual amino-protective groups used for peptide synthesis as the known protective groups, the protective groups used should be easily removed without any cleavage of hydrazide bond in a compound which is synthesized from a β-lysine derivative (I) and 1-methylhydrazinoacetic acid by this procedure.

Suitable monovalent protective groups for amino groups in the β-lysine derivative are alkyloxycarbonyl groups, e.g. tert-butyloxycarbonyl group; cycloalkyloxycarbonyl groups, e.g. cyclohexyloxycarbonyl group; arylalkyloxycarbonyl groups, e.g. benzyloxycarbonyl and p-methoxylbenzyloxycarbonyl groups; and acyl groups especially lower alkanoyl groups, e.g. trifluoroacetyl and o-nitrophenoxyacetyl groups. A divalent protective group is a Schiff base such as salicylidene group. Those protective groups are introduced by known procedure, e.g. using acid halide, acid azide, active ester, etc.

In the preparation of deoxynegamycin the D-β-lysine used as the starting material is made, for example by the treatment of (R,R)-δ-hydroxy-β-lysine with red phosphorus and hydroiodic acid in a sealed tube at 150° C. for 2 hours. The (R,R)-δ-hydroxy-β-lysine is obtained by hydrolysis of negamycin or by synthesis from D-galacturonic acid (J. Am. Chem. Soc., 94, 4353, 1972). Amino-protective groups are introduced into D-β-lysine as described above. For instance, by the treatment of D-β-lysine with benzyl S-4,6-dimethylpyrimidin-2-ylthiolcarbonate in the presence of triethylamine in water-dioxane solution, di-N-benzyloxycarbonyl-D-β-lysine is obtained at excellent yield.

In the preparation of O-methylnegamycin the (R,R)-δ-methoxy-β-lysine used as the starting material is also synthesized from (R,R)-δ-hydroxy-β-lysine and converted directly to the di-N-benzyloxycarbonyl derivative of (R,R)-δ-methoxy-β-lysine. For instance, the aqueous solution of (R,R)-δ-hydroxy-β-lysine is treated with benzyloxycarbonyl chloride in the presence of sodium bicarbonate yielding a lactone of di-N-benzyloxycarbonyl-(R,R)-δ-hydroxy-β-lysine as crystals. The lactone is dissolved in 0.5% hydrogen chloride in methanol, allowed to stand at room temperature and the reaction mixture is concentrated to obtain the methyl ester of di-N-benzyloxycarbonyl-(R,R)-δ-hydroxy-β-lysine as crystals. The ester is reacted with diazomethane in the presence of boron trifluoride etherate in dichloromethane followed by hydrolysis with sodium hydroxide in ethanol to yield di-N-benzyloxycarbonyl-(R,R)-δ-methoxy-β-lysine.

In the coupling process the condensation forming a hydrazide bond with the N-protected β-lysine derivative (I) and 1-methylhydrazinoacetic acid is carried out by known methods for amide synthesis such as methods using dicyclohexylcarbodiimide, mixed anhydride, azide, acid halide, active ester, etc.

For instance, the di-N-benzyloxycarbonyl derivative of the δ-substituted (R,R)-δ-hydroxy-β-lysine is converted to an active ester by treatment with N-hydroxysuccinimide and dicyclohexylcarbodiimide in a nonaqueous solvent. The active ester is condensed with 1-1.5 moles of 1-methylhydrazinoacetic acid in the presence of 1-2.5 moles of sodium bicarbonate in an aqueous solvent. The coupling product thus obtained is treated with 25% hydrogen bromide in acetic acid or hydrogenated with platinum, palladium, etc. as the catalyst to remove the N-benzyloxycarbonyl groups and to synthesize the desired products (II), that is δ-substituted negamycins.

The removal of the protective groups from the coupling product is carried out by a usual method as described above. When the protective groups are alkyloxycarbonyl group or Schiff base the coupling products are hydrolyzed with a weak acid to remove the amino-protective groups.

An arylalkyloxycarbonyl group as the protective group is removed by the treatment with 25% hydrogen bromide in acetic acid, and o-nitrophenoxyacetyl group is easily removed by catalytic hydrogenation with platinum, palladium, etc.

The products are purified with good recovery by ion exchange chromatography using carboxylic cation exchange resins such as "Amberlite CG-50" (Rohm and Haas Co. Ltd., U.S.A.) or "CM-Sephadex C-25" (Pharmacia, Sweden).

O-Methylnegamycin and deoxynegamycin are also able to be derived directly from an amino-protected derivative of negamycin itself as shown in the following formula:

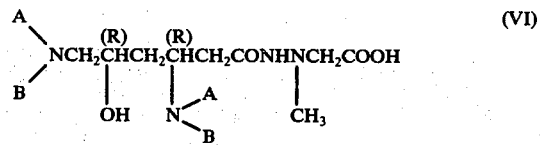

(VI)

wherein A is H and B is a monovalent amino-protective group or A together with B is one divalent amino-protective group. As the amino-protective groups for negamycin, all known amino-protective groups used for D-β-lysine or (R,R)-δ-methoxy-β-lysine above are available in the same procedure. For instance, negamycin is treated with benzyl S-4,6-dimethylpyrimidin-2-ylthiolcarbonate in the presence of triethylamine in a mixture of water-dioxane to obtain di-N-benzyloxycarbonylnegamycin (A = H, B = COOCH₂C₆H₅ in formula VI) in high yield. The benzyloxycarbonyl groups in this derivative are removed by catalytic hydrogenation simultaneously removing halogen atom to prepare deoxynegamycin as described later, and therefore this group is a useful amino-protective group.

O-Methylnegamycin is synthesized from an amino-protected derivative of negamycin (VI) by the same reaction conditions used for O-methylation of amino-protected (R,R)-δ-oxy-β-lysine, that is, treatment with diazomethane in the presence of boron trifluoride etherate in an inert organic solvent such as dichloromethane to obtain an amino-protected derivative of O-methylnegamycin methyl ester as shown by the following formula:

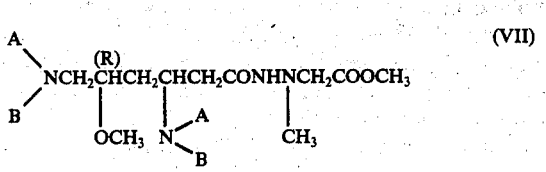

wherein A and B mean the same groups described above. The amino-protective group and methyl ester group are removed by hydrolysis followed by column chromatography with cation exchangers having carboxylic acid as the active group, and if necessary are purified by a column chromatography on silica gel obtaining O-methylnegamycin as the final product.

The present invention also provides the process for the preparation of O-methylnegamycin which comprises conversion of amino-protected derivatives of negamycin (VI)

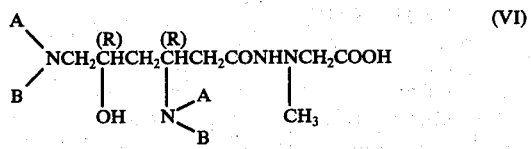

to amino-protected derivative of O-methylnegamycin methyl ester (VII) by reaction with diazomethane in the presence of boron trifluoride etherate followed by removal of the amino-protected groups and methyl ester group from the product (VII).

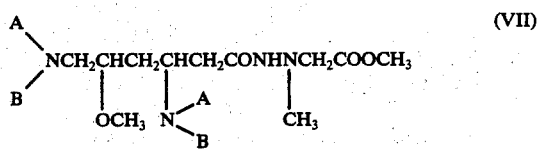

In this procedure the reaction with diazomethane is carried out in an inert organic solvent, for instance, halogenated hydrocarbons such as dichloromethane. The removal of the amino-protective groups and methyl ester group is carried out by ordinary procedures, for instance, by hydrolysis in alkaline condition.

Furthermore, in the synthesis of deoxynegamycin from the amino-protected derivative of negamycin (VI), the only free carboxyl group of amino-protected negamycin is primarily protected with a common ester form, for instance, methyl, ethyl or benzyl ester to obtain an ester of amino-protected negamycin. And then the hydroxyl group at the δ-position of the ester is sulfonylated by treatment with alkylsulfonylating agent such as mesyl chloride, arylsulfonating agent such as p-toluenesulfonyl chloride, or arylmethylsulfonylating agent such as benzylsulfonyl chloride to obtain the sulfonic acid ester derivative as shown by VIII.

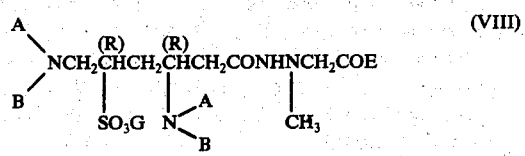

wherein A and B are the same as described in the above; E is an alkyloxy group especially consisting of 1-4 carbon atoms or a benzyloxy group which are ester forming radicals removable easily by hydrolysis to hydroxyl group; G is an alkyl group and especially a lower alkyl group, phenyl group or alkyl substituted phenyl or benzyl group. The product (VIII) is treated with an iodide or bromide of alkali metal such as sodium iodide or sodium bromide and the sulfonyl ester at the δ-position is replaced with iodine or bromine to obtain the δ-iodo- or δ-bromo-derivative which is a mixture of R and S at the δ-position. The iodo- or bromo-derivative in water or methanol or mixed solvent of water and methanol is hydrogenated with palladium or platinum as the catalyst to produce deoxynegamycin derivative by dehalogenation. When the amino-protected group is the benzyloxycarboxyl group as described above the removal of the amino-protected group takes place simultaneously in the above-mentioned catalytic hydrogenation. The remaining amino-protected group is removed by the procedure described above. The ester group of the product is removed by hydrolysis under weakly alkaline conditions and the reaction mixture is purified by column chromatography on cation exchange resin having carboxylic acid as the active group to obtain deoxynegamycin as the final product.

There is further provided by the present invention the process for the preparation of deoxynegamycin whereby an amino-protected derivative of δ-halogenated negamycin ester (IX) is catalytically hydrogenated and the remaining amino-protective group in the compound is removed by a conventional method and the ester forming group (E) is converted to hydroxyl by hydrolysis.

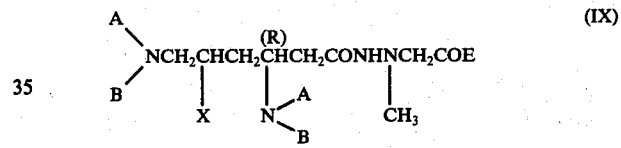

(wherein A is hydrogen and B is a monovalent amino-protective group or A together with B is one divalent amino-protective group, E is an ester forming group which is converted to hydroxyl by hydrolysis, and X is iodine or bromine atom.)

The this procedure an amino-protected derivative of δ-halogenated negamycin ester (IX) is prepared as follows. An amino-protected derivative of negamycin (VI) prepared as above is treated with an agent for esterification such as diazomethane or diazoethane to convert it to negamycin ester derivative (carboxylate). Next the δ-hydroxyl group of the derivative is sulfonylated (—SO₃G) and then halogenated. For instance, the sulfonylation is carried out according to a similar procedure used to prepare an intermediate in the production of 3',4'- dideoxykanamycin B as described in Japan Pat. No. 7595/1975. The reaction to convert the sulfonyl group (—SO₃G) to halogen group (X) by the effect of an iodide or bromide of an alkali metal and the procedure to remove the δ-halogen group by catalytic hydrogenation is also carried out in known manner.

The properties of deoxynegamycin and O-methylnegamycin which are the final products obtained in this invention are as follows:

Deoxynegamycin is a white powder showing d.p. 120°-125° C. $[\alpha]_D^{23} = -5°$ ($c$ 1.5, H$_2$O) and elemental analysis to coincide with the theoretical value for C$_9$H$_{20}$N$_4$O$_3$·H$_2$O (C 43.18%, H 8.86%, N 22.39%). On silica gel thin layer chromatography (Art. 5721, Merck Co., Germany) developed with n-butanol-ethanolchloroform-17% aqueous ammonia (4:5:2:5 by volume) it gives a single spot (ninhydrin) at Rf 0.14.

O-Methylnegamycin is a white powder showing d.p. 137°–140° C. $[\alpha]_D^{22} = -3°$ (c 1.5, $H_2O$), and elemental analysis to coincide with the theoretical value for $C_{10}H_{22}N_4O_4 \cdot H_2O$ (C 42.84%, H 8.63%, N 19.99%). On the tlc described above it gives a single spot at Rf 0.33. As shown in the table, those two novel derivatives of negamycin inhibited the growth of Gram-positive and Gram-negative bacteria. Those two compounds were completely stable in both aqueous or 0.02N HCl aqueous solution at 37° C. for one month while negamycin as the control was reduced in its activity to 63% in aqueous solution and to 50% in 0.02N HCl aqueous solution. Those two compounds are low in toxicity ($LD_{50}$ of both in mice, i.v., >200 mg./kg.) and are expected to be used in the chemotherapy of infections caused by various Gram-positive and Gram-negative bacteria.

TABLE

Antimicrobial Spectra of O-Methylnegamycin and Deoxynegamycin

| Test Organisms | Minimum Inhibitory Concentrations*(Mcg./ml.) | |
|---|---|---|
|  | O-Methyl-negamycin | Deoxy-negamycin |
| Staphylococcus aureus FDA209P | 12.5 | 25 |
| Staphylococcus aureus Smith | 6.25 | 6.25 |
| Sarcina lutea PCI1001 | 25 | >100 |
| Micrococcus flavus FDA16 | 50 | 50 |
| Bacillus subtilis NRRL B-558 | 50 | 100 |
| Mycobacterium smegmatis ATC607 | 25 | 50 |
| Escherichia coli NIHJ | 6.25 | 6.25 |
| Escherichia coli K-12 | 3.13 | 3.13 |
| Escherichia coli K-12 ML1629 | 1.56 | 3.13 |
| Salmonella typhi T-63 | 1.56 | 0.78 |
| Proteus vulgaris OX-19 | 1.56 | 3.13 |
| Proteus rettgeri GN311 | 6.25 | 6.25 |
| Proteus rettgeri GN466 | 3.13 | 3.13 |
| Serratia marcescens | 25 | 25 |
| Klebsiella pneumoniae PCI602 | 6.25 | 6.25 |
| Pseudomonas fluorescens | 1.56 | 3.13 |
| Pseudomonas aeruginosa A3 | 12.5 | 25 |
| Pseudomonas aeruginosa No. 12 | 25 | 50 |

*Minimum inhibitory concentrations were determined on a 0.5% peptone agar by incubation at 37° C. for 17 hours.

DESCRIPTION OF THE PREFERRED EMBODIMENTS

EXAMPLE 1 a. Synthesis of Di-N-benzyloxycarbonyl-D-β-lysine

To a solution containing 100 mg. (0.69 mmole) D-δ-lysine ($[\alpha]_D^{25} = -22.5°$ (c 0.8, 1N HCl) in 1 ml. of water, 104 mg. (1.0 mmole) of triethylamine at first and then a solution containing 410 mg. (1.5 mmoles) benzyl S-4,6-dimethylpyrimidin-2-ylthiolcarbonate (Kokusan Chemical Works, Tokyo) in 1 ml. of dioxane were added and stirred at 30° C. for 17 hours. To the reaction mixture 3 ml. of water was added and the mixture was washed with 6 ml. of ether. The aqueous layer was adjusted to pH 2 with 6N HCl, saturated with sodium chloride and extracted with 13 ml. of ethyl acetate. The ethyl acetate layer was washed with 4 ml. of 5% HCl in water saturated with sodium chloride and with 4 ml. of water saturated with sodium chloride, dried with anhydrous sodium sulfate and concentrated to dryness under reduced pressure to obtain 219 mg. of di-N-benzyloxycarbonyl-D-β-lysine as colorless crystals, d.p. 149°–151° C., $[\alpha]_D^{26} = +6°$ (c 1.3, MeOH), 73% yield.

b. Synthesis of Deoxynegamycin

To a solution containing 79 mg. of di-N-benzyloxycarbonyl-D-β-lysine obtained in Example 1 (a) dissolved in 3 ml. of 1,2-dimethoxyethane, 22 mg. (0.19 mmole) of N-hydroxysuccinimide and 39 mg. (0.19 mmole) of dicyclohexylcarbodiimide were added under ice-cooling. After the reaction mixture was allowed to stand at 5° C. for 17 hours crystals of dicyclohexylurea deposited and were removed by filtration and the filtrate was concentrated to dryness to obtain 97 mg. of N-hydroxysuccinimide ester of di-N-benzyloxycarbonyl-D-β-lysine as colorless crystals.

A solution containing the crystals obtained in the above dissolved in 2 ml. of 1,2-dimethoxyethane was gradually added to a solution containing 19.8 mg. (0.19 mmole) of 1-methylhydrazinoacetic acid and 32 mg. (0.38 mmole) of sodium bicarbonate in 0.5 ml. of water under stirring at room temperature. After 18 hours stirring the reaction mixture was concentrated to dryness under reduced pressure and the residue was dissolved in 0.5 ml. of water. To this solution cooled in ice was added 0.42 ml. of 1N HCl forming a white precipitate. The precipitate was collected by filtration, washed with water and dried to obtain 108 mg. of di-N-benzyloxycarbonyldeoxynegamycin as a white powder.

The white powder was dissolved in a mixture containing 1 ml. of acetic acid, 0.8 ml. methanol and 0.2 ml. water. To the solution was added 50 mg. of 5% palladium-carbon. After the mixture was stirred for 3 hours under an atmosphere of hydrogen the catalyst was removed by filtration and the filtrate was concentrated to dryness. The residue was dissolved in 2 ml. of water adjusted to pH 8.4 with 5N ammonia-water and passed through and adsorbed on a column containing 8.5 ml. Amberlite CG-50 ($NH_4^{30}$) resin. The column was washed with 20 ml. water and eluted with 90 ml. of 1% ammonia-water. The eluate was collected as 1 ml. fractions. Fractions No. 57–62 having antibacterial activity to E. coli K-12 were collected and concentrated to dryness to obtain 20.5 mg. of deoxynegamycin as a white powder. Yield was 47%.

EXAMPLE 2 a. Synthesis of Di-N-benzyloxycarbonyl-(R,R)-δ-hydroxy-β-lysine Methyl Ester

To a solution containing 26 g. of (R,R)-δ-hydroxy-β-lysine and 63 g. of sodium bicarbonate in 450 ml. of water was added dropwise 77 g. of benzyloxycarbonyl chloride at room temperature. After stirring for another 2 hours the mixture was allowed to stand at 5° C. for 18 hours. Crystals deposited and were collected by filtration, washed with 200 ml. of water and with 350 ml. of ether and dried to obtain 44.3g. of di-N-benzyloxycarbonyl-(R,R)-δ-hydroxy-β-lysine lactone as colorless crystals. m.p. 128°–130° C., $[\alpha]_D^{22} = -13°$ (c 3.4, chloroform), 70% yield. The crystals (34.2 g.) were dissolved in 360 ml. of 0.5% $HCl-CH_3OH$ and allowed to stand at room temperature for 16 hours. The reaction mixture was concentrated and the crystals which deposited were recrystallized from a mixture of methanol-ether to obtain 28.3 g. of di-N-benzyloxycarbonyl-(R,R)-δ-hydroxy-β-lysine methyl ester as colorless crystals. m.p. 111°–112° C., $[\alpha]_D^{28} = +11°$ (c 1.2, chloroform), 77% yield.

b. Synthesis of Di-N-benzyloxycarbonyl-(R,R)-δ-methoxy-β-lysine

The 266 mg. (0.6 mmole) of di-N-benzyloxycarbonyl-(R,R)-δ-hydroxy-β-lysine methyl ester obtained in Example 2 (a) was dissolved in 4 ml. of dichloromethane. To that solution under stirring at ice-cooling was added 17 mg. (0.12 mmole) of boron trifluoride etherate and to the mixture 1.5% diazomethane-ether was added until the yellow color remained in the reaction mixture (4 hours). After stirring at room temperature for 16 hours the reaction mixture was washed with 10 ml. of 10% sodium bicarbonate-water and 20 ml. of water successively and the solvent layer was dehydrated with anhydrous sodium sulfate and concentrated to dryness under reduced pressure yielding 295 mg. of pale yellow oily material. The oily material was chromatographed on a column containing 30 g. of silica gel developed with benzene-methyl ethyl ketone (10:1 by volume) and collected in 9 ml. fractions. Fractions No. 31–59 were collected and concentrated to dryness yielding 87 mg. of di-N-benzyloxycabonyl-(R,R)-δ-methoxy-β-lysine methyl ester as a colorless oil. 32% yield.

To a solution containing 85 mg. (0.19 mmole) of the oil in 0.5 ml. of ethanol, 0.22 ml. of 1N NaOH was added. After allowing to stand at room temperature for 4 hours the mixture was acidified by the addition of 0.28 ml. of 1N HCl and extracted with 3 ml. of ethyl acetate. The ethyl acetate layer was washed with 1 ml. of water, dehydrated with anhydrous sodium sulfate and concentrated to dryness yielding 80 mg. of di-N-benzyloxycarbonyl-(R,R)-δ-methoxy-β-lysine as a colorless oil. 98% yield.

c. Synthesis of O-Methylnegamycin

To a solution containing 80 mg. (0.18 mmole) of di-N-benzyloxycarbonyl-(R,R)-δ-methoxy-β-lysine which was obtained in Example 2 (b), in 1.6 ml. of 1,2-dimethoxyethane, 21 mg. (0.18 mmole) of N-hydroxy-succinimide were added under ice cooling. After the reaction mixture was allowed to stand at 5° C. for 17 hours dicyclohexylurea appeared and was removed by filtration and the filtrate was concentrated to dryness yielding 98 mg. of N-hydroxy succinimide ester of di-N-benzyloxycarbonyl-(R,R)-δ-methoxy-β-lysine as a colorless oil.

A solution of the oil in 1.5 ml. of 1,2-dimethoxyethane was gradually added at room temperature under stirring to a solution containing 18.7 mg. (0.18 mmole) of 1-methylhydrazinoacetic acid and 30 mg. (0.36 mmole) of sodium bicarbonate in 0.5 ml. of water. After stirring for 20 hours the reaction mixture was concentrated to dryness, dissolved in 0.5 ml. of water and a white powder was precipitated by the addition of 0.4 ml. 1N HCl under ice-cooling. The precipitate was dissolved in 3 ml. of ethyl acetate and washed with 0.5 ml. of water. The ethyl acetate layer was dehydrated with anhydrous sodium sulfate and concentrated to dryness yielding 94 mg. of di-N-benzyloxycarbonyl-O-methylnegamycin as a white powder.

To a solution containing the white powder obtained above in a mixture containing 1 ml. of acetic acid, 0.8 ml. of methanol and 0.2 ml. of water, 24 mg. of 5% palladium-carbon was added and the mixture was stirred with hydrogen gas for 4 hours. After removal of catalyst by filtration the filtrate was concentrated to dryness. The residue was dissolved in 2 ml. of water, adjusted to pH 8.8 with 5N ammonia and charged into a column containing 10 ml. of Amberlite CG-50 (NH+4). The column was washed with 20 ml. of water and eluted with 100 ml. of 0.1% ammonia-water collecting 1 ml. fractions. Fractions No. 45–57 having antibacterial activity were combined and concentrated under reduced pressure to dryness to provide 20.8 mg. of O-methylnegamycin as a white powder. 44% yield.

EXAMPLE 3 a. Synthesis of Di-N-benzyloxycarbonylnegamycin

To a solution containing 4 g. (16.1 mmoles) of negamycin in 20 ml. of water and 2.44 g. (24.2 mmoles) of triethylamine, 9.72 g. (35.5 mmoles) of benzyl S-4,6-dimethylpyrimidin-2-ylthiolcarbonate on 20 ml. of dioxane was added and the reaction mixture was stirred at room temperature for 17 hours. To the reaction mixture 30 ml. of water was added and the mixture was washed with two portions of 60 ml. of ethyl acetate. The aqueous layer was adjusted to pH 2 with 6N HCl and extracted with two portions of 60 ml. of ethyl acetate after saturation with sodium chloride. The ethyl acetate layer was washed with 80 ml. of water saturated with sodium chloride dehydrated with anhydrous sodium sulfate and concentrated to dryness under reduced pressure to yield 7.6 g. of di-N-benzyloxycarbonylnegamycin as a white powder. d.p. 110°–113° C., $[\alpha]^{26}_D = +4.2°$ (c 6.3, $CH_3OH$), 92% yield.

b. Synthesis of O-Methylnegamycin

To a solution containing 449 mg. (0.87 mmole) of di-N-benzyloxycarbonylnegamycin which was obtained in Example 3(a), in 4.5 ml. of dichloromethane, 62 mg. (0.44 mmole) of boron trifluoride etherate was added with ice-cooling and stirring followed by the addition of 1.5% diazomethane-ether solution until the yellow color of the reaction mixture remained (for 2 hours). The reaction mixture was concentrated to dryness yielding di-N-benzyloxycarbonyl-O-methylnegamycin methyl ester as a crude powder. The powder was dissolved in 5 ml. of 25% hydrogen bromide-acetic acid and stirred at room temperature for 20 minutes to remove the amino-protective groups.

To the solution 50 ml. of ethyl ether was added and a precipitate appeared which was collected by filtration, washed with 20 ml. of ethyl ether and dried to obtain a yellow powder. The powder was dissolved with 20 ml. of water, adjusted to pH 8.8–9.0 with 5N ammonia-water and charged into a column containing 40 ml. of Amberlite CG-50 (NH+4). The column was washed with 80 ml. of water and eluted with 200 ml. of 0.9% ammonia-water collecting 4 ml. fractions. Fractions No. 32–34 giving positive ninhydrin were collected and concentrated to dryness under reduced pressure to yield 141 mg. of O-methylnegamycin as a crude powder. The crude powder was charged into a column of silica gel (14 g.) and developed with n-butanol-ethanol-chloroform-17% ammonia in water (4:52:3 by volume) collecting 4 ml. fractions. Fractions No. 24–28 having positive ninhydrin reaction and antibacterial activity versus E. coli K-12 were combined and concentrated to dryness under reduced pressure to yield 30 mg. of O-methylnegamycin as a white powder. 13% yield.

EXAMPLE 4 a. Synthesis of Di-N-benzyloxycarbonylnegamycin Methyl Ester

To a solution containing 6 g. (11.6 mmoles) of di-N-benzyloxycarbonylnegamycin which was obtained in Example 3 (a), in 120 ml. of methanol, 1.5% diazomethane-ethanol-ether solution was added until the yellow color of the mixture remained. After stirring for 45 minutes the reaction mixture was concentrated to dryness under reduced pressure to yield 5.98 g. of di-N-benzyloxycarbonylnegamycin methyl ester. d.p. 107°-112° C., $[\alpha]_D{}^{26} = +4.0°$ (c 5.0, $CH_3OH$), 97% yield.

b. Synthesis of Deoxynegamycin

To a solution containing 5.98 g. (11.3 mmoles) of di-N-benzyloxycarbonylnegamycin methyl ester which was obtained in Example 4 (a), in 150 ml. of pyridine a solution containing 6.43 g. (56.4 mmoles) of methanesulfonyl chloride in 150 ml. of pyridine was added with ice-cooling for 15 minutes. After stirring at room temperature for 5 hours the reaction mixture was diluted with 150 ml. of ice water and extracted with 240 ml. of chloroform. The chloroform layer was washed successively with 60 ml. portions of 0.5M sodium bisulfite, water, 1M sodium bicarbonate and water. After dehydration with anhydrous sodium sulfate the chloroform solution was concentrated to dryness under reduced pressure yielding 6.17 g. (10.1 mmoles) of di-N-benzyloxycarbonyl-O-methanesulfonylnegamycin methyl ester as a pale yellow powder.

To a solution containing 4.9 g. (8.1 mmoles) of the pale yellow powder so obtained in 225 ml. of acetone, 7.2 g. (48 mmoles) of sodium iodide, which was thoroughly dried at 50°-60° C. overnight, was added. The mixture was refluxed at 65° C. for 15 hours, diluted with 1,120 ml. of water and extracted with 1,350 ml. of ethyl acetate. The ethyl acetate layer was washed with 450 ml. of water, dehydrated with anhydrous sodium sulfate and concentrated to dryness under reduced pressure to yield 3.98 g. of a pale yellow powder. The powder was subjected to a column chromatography on silica gel (400 g.) using benzene-methyl ethyl ketone (1:1 by volume) as the developing solvent. The eluate was collected in 18 ml. fractions and Fractions No. 77–170 were combined and concentrated to dryness under reduced pressure to yield 1.3 g. (2 mmoles) of δ-iodo-derivative (a mixture of 2 kinds of stereoisomer). 22% yield.

To a solution containing 937 mg. (1.46 mmoles) of the δ-iodo-derivative thus obtained in 20 ml. of methanol and 8 ml. of water, 10 g. of 5% palladiumbarium carbonate was added at room temperature under stirring and introduction of hydrogen gas to carry out simultaneously dehalogenation and removal of benzyloxycarbonyl groups. The catalyst was removed by filtration and the filtrate was concentrated to dryness under reduced pressure. The residue was dissolved in 16 ml. of water, adjusted to pH 9.2–9.4 with 5N ammonia-water and charged into a column containing 97 ml. of Amberlite CG-50 ($NH_4{}^{+4}$). After washing with water the column was eluted with 650 ml. of 0.2% ammonia-water and the eluate was collected in 5 ml. fractions. Fractions No. 20–50 having antibacterial activity versus E. coli K-12 and positive ninhydrin reaction were combined and concentrated to dryness under reduced pressure to yield 95 mg. of deoxynegamycin as a white powder. 28% yield.

We claim:

1. The compound having the formula

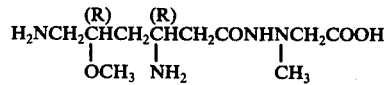

wherein each symbol (R) indicates that the carbon atom beneath said symbol has the rectus configuration, or a nontoxic salt thereof.

2. The compound of claim 1 having the formula

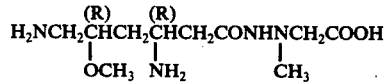

wherein each symbol (R) indicates that the carbon atom beneath said symbol has the rectus configuration.

3. A nontoxic, pharmaceutically acceptable acid addition salt of the compound of claim 2.

* * * * *